United States Patent [19]

Moser et al.

[11] Patent Number: 5,674,072
[45] Date of Patent: Oct. 7, 1997

[54] TWO-PHASE TOOTH IMPLANT

[75] Inventors: Walter Moser, Kaufdorf, Switzerland; Georg Hubertus Nentwig, Frankfurt, Germany

[73] Assignee: Degussa Aktiengesellschaft, Germany

[21] Appl. No.: 544,319

[22] Filed: Oct. 17, 1995

[30] Foreign Application Priority Data

Oct. 17, 1994 [CH] Switzerland .................. 03106/94

[51] Int. Cl.$^6$ ..................................... A61C 8/00
[52] U.S. Cl. .............................. 433/173; 433/174
[58] Field of Search ...................... 433/172, 173, 433/174, 175, 176

[56] References Cited

U.S. PATENT DOCUMENTS

| | | | |
|---|---|---|---|
| 4,758,160 | 7/1988 | Ismail | 433/174 |
| 5,030,095 | 7/1991 | Niznick | 433/174 |
| 5,213,500 | 5/1993 | Salazar et al. | 433/173 |
| 5,433,606 | 7/1995 | Niznick et al. | 433/173 |
| 5,492,470 | 2/1996 | Anders | 433/173 |
| 5,509,804 | 4/1996 | Arzt | 433/173 |

*Primary Examiner*—Cary E. O'Connor
*Attorney, Agent, or Firm*—Beveridge, DeGrandi, Weilacher & Young, L.L.P.

[57] ABSTRACT

Mechanical joining of a two-phase tooth implant, consisting of two components which are joined by means of a conical pin projecting into a conical sleeve, the cone pairing being realized within the self-locking region and the cone pin being penetrated by a centrally aligned, tension screw reduced diameter which tensions the pair of cones against each other. The design permits the two implant components in a two-phase tooth implant to be steplessly positioned in the circumferential direction and to be joined in an anti-rotation, gap-free joint. The required degree of miniaturization, with a sufficient component strength, is achieved through the use of a cone combination in the self-locking region and through the use of a tension screw in the region of the cone joint. By these means, the mechanical, aesthetic and hygienic requirements for a two-phase tooth implant are better fulfilled than in the case of the known designs.

11 Claims, 1 Drawing Sheet

U.S. Patent
Oct. 7, 1997
5,674,072
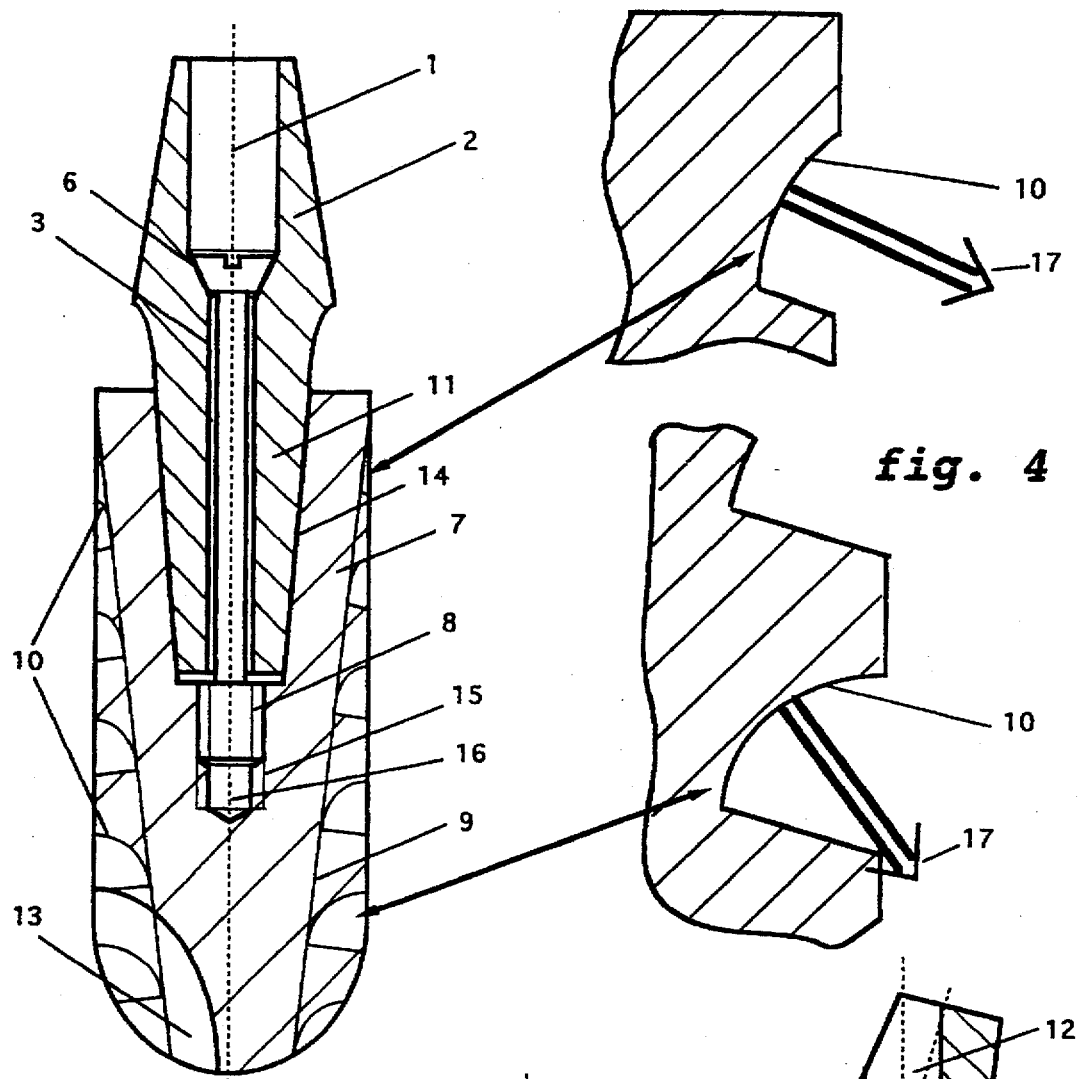
fig. 1
fig. 4
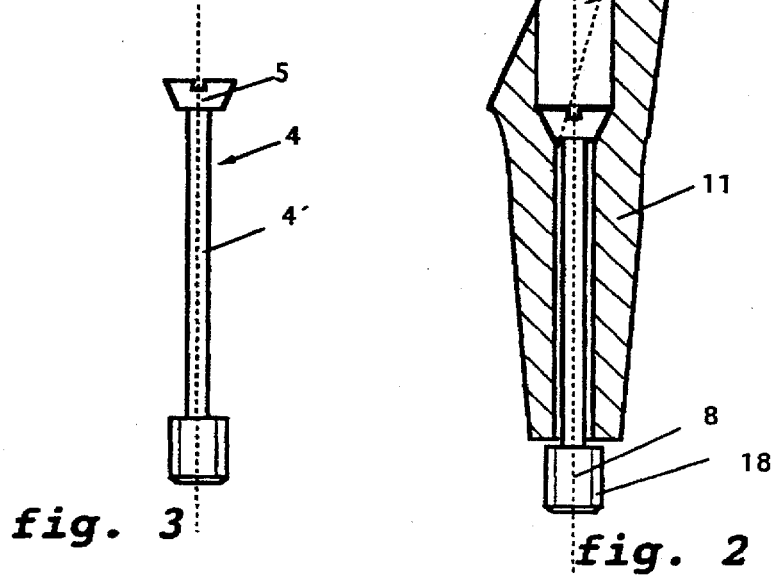
fig. 3
fig. 2

TWO-PHASE TOOTH IMPLANT

INTRODUCTION AND BACKGROUND

The present invention concerns a two-phase tooth implant with a first implant component, having a central seating opening, which is inserted into the jawbone, and a second implant component which carries the dental structure and includes a conical seating element for the dental prosthesis and a part which fits into the seating opening of the first implant component.

Intra-ossal tooth implants are used for anchoring individual teeth or dental prostheses. A distinction is made between single-phase and two-phase systems, preference being given to two-phase systems which, concealed under the gum in a first phase, are able to osseointegrate safely without stress and are only equipped with the part carrying the artificial tooth or dental prosthesis in the second, or actual load-application phase. The part anchored in the jawbone has an appropriate screw profile or other macroscopic surface structures so that a firm primary anchorage is achieved. Metal and ceramic materials are known to be suitable.

Great importance pertains to the mechanical joining of the two implant components, the part anchored in the jawbone and the part which is coupled to it and passes through the gum, projecting into the mouth cavity. General requirements for such a joining element are the absorption and transfer of high masticatory forces with minimum dimensions and a joint between the two implant components which is free from play and as impervious to bacteria as possible. Such a joint, based on a cone, is known from U.S. Pat. No. 4,772,204 (WO 85/02337).

Anatomical, biomechanical and aesthetic requirements can necessitate the use of a mechanical joint having an angle between the part anchored in the bone and the part carrying the dental structure which projects into the mouth cavity. The angle enclosed between the two implant components increases the demands on such a joining element with respect to their twisting towards each other and their positional accuracy. These requirements would not be met by a joint effected by a simple threaded screw fitting as described, for example, in DE 24 54 414 and DE 24 13 883. Positive joints, such as true-fitting hexagonal or octagonal geometries, are primarily selected to fulfil this function. Such positive joints are described, for example, in U.S. Pat. No. 5,125,840 (DE 40 28 855), U.S. Pat. No. 5,199,873 (EP 0 438 048), DE 41 27 839, EP 0 504 119, U.S. Pat. No. 5,069,622 (EP 0 323 421) and WO 94/06367.

In DE 40 28 855 (U.S. Pat. No. 5,125,840) there is proposed a distance sleeve with a positive-fit interlocking-face denticulation which provides for a torsion-free joint between the two implant components, there being described four possible positions in this structure and this denticulation being located inside the part inserted in the jawbone. Provided that the rotational forces caused by masticatory stresses are introduced via this sleeve and not via the implant stud screwed into it which is not rotation-proof, this joint forms an anti-rotation device such as that required, for example, for a single artificial denture. For design and production reasons, this arrangement does not provide a gap-free joint.

In DE 40 28 857 (U.S. Pat. No. 5,122,059) relating to the same implant, an anti-torsion device, to be effected by means of a deformed intermediate ring, is proposed as an alternative to the positive geometric fit. The force applied in assembling a screwed joint causes the two faces of the intermediate ring to be compressed as the parts which are to be joined together are raised or lowered. This rotation lock is subject to masticatory forces and the effect of the torsion lock can decrease due to further deformation of the intermediate ring under the substantial masticatory stresses. Due to the limited geometric positive fit of the possible deformation and the inherent softness of the ring, this concept offers a substantially lesser locking effect against loosening of the joined components due to turning than the geometric positive fit. This joint also, like the concept described in DE 40 28 855, cannot be made gap-free.

The anti-torsion joints proposed in WO 94/06367, EP 0 438 048, DE 40 22 753 and DE 41 27 839 are likewise based on interlocking positive-fit joints with the disadvantage that the rotational position is defined in steps and that this joint cannot be made gap-free. In the arrangement illustrated in EP 0 438 048, two positive-fit joints are aligned in succession, and although it is possible to increase the fineness of the positional adjustment by this means, again in this case the rotational position of the part which is inserted into the bone and becomes firmly anchored there after the healing-in phase predetermines the final position of the support projecting into the mouth to which the dental prosthesis is applied.

A further problem with all positive-fit rotation locks is the necessity of producing these joints, even in series production, so that all parts fit with each other without play. Due to the pulsating stress caused by the masticatory load applied with large forces and at a high cyclic rate, there is a danger that a small amount of play present in the positive fit of the assembled structure will become larger as the functional period increases and that this in turn will result in disintegration of the entire dental structure. For this reason, U.S. Pat. No. 5,328,371 (EP 0 593 926) describes an element which deforms under the initial stress resulting from assembly so as to compensate for this play in a hexagonal structure. This elastically and/or plastically deforming element is again subject to the applied masticatory load, which again involves the risk of loosening of the joint.

Disadvantages of all positive-fit joints known hitherto therefore include the limited number of possible positions, the fact that a gap-free construction of these joining elements is attainable only at great expense and, likewise, the great difficulty in producing these structures free from play. The rotational position of the implant, however, must be determined as early as the surgical insertion stage with respect to the inclination of the seating stud due to the fact that, in the case of the joints described, such as for example the octagonal joint, it is then only possible to effect positioning steps of 45° after the implant has become healed into the bone. In order for a gap-free joint to be achieved in all positive-fit centerings, all possible mutually contacting surface pairs must be made to fit exactly, which requires an extremely precise production technology.

Joints which are free of both gaps and play and which are capable of transferring high axial forces and high flexural forces can be produced by means of cone joints with a fixed thread, as described in WO 85/02337. However, due to the limited possible insertion force, resulting from the fixed thread, these are not suitable for transferring high forces in a circumferential direction, such as those which occur in the case of application as a single tooth implant or in the case of an angle being included between the implant components.

The combination, proposed in WO 94/06396, of a positive-fit and a non-positive cone joint by means of a joining sleeve does permit stepless adjustment of the rotational position, but this combination includes the risks, described above, of play and gaps in the joint. In addition, a joint made in this way will limit the attainment of the smallest implant diameter that is possible, for a given masticatory load, due to the size of the structure required, necessitating a limited implant indication.

SUMMARY OF THE INVENTION

An object of the present invention is to provide a two-phase, gap-free tooth implant capable of rotationally stable and circumferentially stepless orientation, with a first implant component, having a central seating opening, which is inserted into the jawbone, and a second implant component which carries the dental structure and includes a conical seating element for the dental prosthesis and a part which fits into the central seating opening of the first implant component. This stepless joint, which is continuous in the circumferential direction of the implant element, is capable of coping with the high mechanical stresses due to the forces of mastication in spite of its very small dimensions. The joint remains permanently free from gaps with, in particular, the rotational forces occurring in the case of an angle being included between the axes of the two implant components being reliably absorbed and transferred.

This object and others are achieved, according to the invention, in that the central seating opening in the first implant component is conical and the part of the second implant component which fits into it is a matching cone, the second implant component having a central bore passing through it within which is located the cylindrical shaft of a tension screw being of reduced diameter in its central part and which has a widened end with an outer fastening thread which fits into the inner thread of a blind bore located in an extension of the seating opening.

BRIEF DESCRIPTION OF THE DRAWINGS

The present invention will be further understood with reference to the drawings, wherein:

FIG. 1 is a schematic view of the cone joint according to the invention, with a central tension screw;

FIG. 2 is a schematic view of the top component (second implant) of the cone joint according to the invention, with a central tension screw with an angle included between the two implant components; and FIG. 3 is a schematic view of the detail of the tension screw with a reduced cross-section in the area of the joining cone through which the screw passes when in place.

FIG. 4 is a schematic view of the threaded flanks of the first implant component that have a varying form to lower the stresses in the cervical region of the bone fixation.

DETAILED DESCRIPTION OF THE INVENTION

According to a more detailed aspect of the invention, a two-phase tooth implant is disclosed, which is free of gaps and capable of being steplessly positioned in its rotational orientation, including a first implant component, having a central seating opening, which is capable of being inserted into a jawbone, and a second implant component which carries a dental structure and includes a conical seating element for the dental prosthesis and a part which fits into said central seating opening of said first implant component. The central seating opening in said first implant component is conical in shape and the part of said second implant component which fits into the central seating opening in the first implant component is a matching cone which mates with the opening. The second implant component has a central bore passing through said second implant component. Within this central bore is located the tapered cylindrical shaft of reduced diameter of a tension screw. The screw has a widened end with an outer fastening thread which fits into the inner thread of a blind bore. The central seating opening of said first implant component has an extended region beyond the depth necessary to accomodate the tapered cone of the second implant component and which region accomodates the tip of the screw.

It is preferable that the axes of the two conical parts of the second implant component are in alignment with each other or, alternatively, that these axes form an angle.

It is furthermore advantageous if the central bore of the second implant component is widened at the end directed towards the mouth cavity so that the head of the tension screw is seated within it.

It has proved advantageous if the angle of the conical seating opening of the first implant component and the angle of the part of the second implant component fitting within it are selected so as to produce a self-locking cone joint. The angles are therefore normally of identical sizes.

It is also advantageous if the widened end of the tension screw is irreversibly connected to the end of its long shaft and by this means the tension screw is captured within the second implant component.

For good primary stability and successful longterm fixation it is advantageous if the first implant component has an essentially cylindrical outer form with a spherically rounded end and a thread of specially adapted geometry (e.g., with a varying flank depth), the form of the thread flanks varying continuously upwards from the end embedded in the bone towards the central seating opening, the thread flank which points upwards towards the seating opening being formed as a plane surface and the thread flank which points downwards, varying in form, having a curved, concave shape (10). Special thread (see for example DE 36 42 901) for dental implants which are inserted in the jaw bone are characterized in that the thread over its length has a variable curve form towards the apex of the flanks of the treads so that in actual loading during chewing there is obtained a significant lowering of the force on the surface and thereby a reduction in tension in the bone in the cervical region.

The cone joint designed according to the invention enables the implant components to be firmly joined together in a gap-free, rotationally stable joint due to the cone angle being matched to the friction ratios of the cone joint and to the central tension screw being aligned within the axis of the cone, the rotational position of the two implant components being freely and steplessly selectable during assembly. In order to accommodate to the constricted space conditions and to meet the mechanical requirements of the joint, the tension screw is of reduced diameter in the region of the through passage of the cone; i.e., the bore of the second implant, absorbing the axial and bending forces and is widened in the region of the thread absorbing the tensile forces. For the purpose of achieving a seal, it is preferable if the seating of the tension screw head is also conical in form, the frictional action of the tension screw cone being significantly less than the frictional action of the joining cone. The fact that the thin tension screw lies close to the neutral axis of the cone joint which is subjected to bending load means that the load-bearing capacity of the cone joint is weakened only by an insignificant amount. It is possible to achieve an optimum load capacity of the cone joint with respect to axial and bending forces and forces in the circumferential direction through matching of the angle of the joining cone, the shaft cross-section of the tension screw and the cone angle under the screw head. The cone angle is preferably selected so that the joint is located in the self-locking region and so that the forces occurring in application never exceed this self-locking region, with the result that no additional operational forces are transferred to the tension screw.

It is possible to achieve an increased sealing effect in the cone entry region or to influence the tension of the implant part anchored in the bone by the selection of small angle variations between the outer and inner cones. If the angle of the outer cone is slightly larger than that of the inner cone, an increased sealing effect is achieved in the cone entry region, in the sense of a pinched edge. If the angle of the outer cone is slightly smaller than that of the inner cone, tensions in the part embedded in the bone caused by the cone joint are displaced towards the center of the component. The difference in angle to achieve either an increased sealing effect or the transfer of stresses in the first implant component towards its center is in the area of less than 0.5 degrees.

The first and second implant may be made of pure titanium or titanium alloys approved for dental applications such as Ti6Al4V alloy. Because of high stresses, the central tension screw should be made of high strength alloys approved for dental applications such as titanium alloys or cobalt based alloys. Such alloys are known in the art.

As shown in FIGS. 1 and 2, the second implant component (11), which acts as a joining element, is bored completely through along its axis (1), the bore (3) being widened in the region of the end (2) projecting into the mouth cavity; (16) is the end of the central bore of the first implant component (7). The diameter of the widened bore matches the head (5) of a central tension screw (4). In the upper region of the central bore (12) the diameter is slightly larger than the shaft diameter of the central tension screw (4). The head (5) of this central tension screw (4) is located in the widened bore of the end (2) projecting into the mouth cavity. The cone angle of the head seating (6) is selected so as to render possible both a secure sealing of the screw head (5) on the seating and a sufficient pretensioning of the tension screw (4). The angles of the inner cone of the first implant component (7) anchored in the bone and of the conical pin which is to be mechanically fixed within it are identical or matched to each other. This angle is constructed so as to produce a self-locking of the cone joint for the possible combinations of axial forces, bending forces and forces in the circumferential direction. The tension screw (4) terminates in an increasing cross-section at its lower end (8) which has a fastening thread (18) by means of which the tension screw (4) and, consequently, the joining cone, is tensioned against the first implant component (7) anchored in the bone.

The first implant component (7) is primarily anchored in the bone, being surrounded and held stable by the bone structure during the healing-in phase, by means of a special outer thread (9), the flank geometry (10) of which varies over the length of the implant. The special form of the outer thread is such that the masticatory forces (17) are dispersed in a direction perpendicular to the surfaces of the thread flanks and directed into the depth of the bone mass in correspondence with the form of these flanks which varies over the length of the implant. This positive fit is supported by recesses (13) at the lower end and by a microstructure on the entire surface which comes into contact with the spongy bone mass. Inner thread (15) matches with the thread of the central tension screw.

The second implant component (11) has the form of two cylindrical truncated cones, one mounted on the other by their bases, having axes which can be aligned to each other or enclose an angle (12), one of the two cones fitting into the central seating opening (14) of the first implant component (7) anchored in the bone, while the other cone supports the dental prosthesis.

In order to allow for both the mechanical stresses, as a pretensioned element, and the requirements of miniaturization, the tension screw (4) is of reduced diameter in the its central region (4').

The central reduced diameter of the tension screw (4) is also necessary in order to achieve a sufficient flexural resistance of the cone and a sufficient bearing length of the interconnected cone pair with the small diameter of the implant and the associated small available structural volume of the cone joint. At the same time, this provides for a sufficiently large seating of the screw head (5) and a sufficiently large diameter of the fastening thread (18) at the lower end (8) of the tension screw (4).

A possibility for production of the reduced central diameter is offered by joining the lower end (8) or, alternatively, the screw head (5), to the tension screw (4) by welding. The tension screw (4) is joined to the joining cone so as to be incapable of loosening due to the fact that the bore diameter (3) is smaller than the screw head (5) and the thread (18). In the case of use of a titanium implant material, this joint can be effected by means, for example, of laser welding. Alternatively, other material-closing joining methods, or a positive-fit joint, e.g. a thread, may be used.

For the purpose of producing the intended cohesive friction of the cone joint which is of particular importance for absorption of the operational forces acting in the circumferential direction in combinations which enclose an angle (12) between the two implant components, the central tension screw (4) is pretensioned by a defined quantity by means of a torque wrench which is appropriately miniaturized for use within the mouth. The use of a torque wrench ensures that the two components are joined together in a reproducible, gap-free and therefore germproof joint.

By means of a standardized, equally dimensioned cone joint, it is possible for parts which are to be anchored in the jawbone and which are of widely differing geometry, e.g. having different diameters and lengths, to be freely combined with parts which project into the mouth cavity, so that the individual conditions of the patient to be treated are accommodated to a high degree with a relatively small number of components.

Further variations and modifications of the foregoing will be apparent to those skilled in the art and such variations and modifications are intended to be encompassed by the claims that are appended hereto.

Swiss Priority Application 03106/94-0, filed on 17 Oct. 1994, is relied on and incorporated by reference in its entirety. The U.S. Patents cited herein are incorporated by reference in their entirety.

We claim:

1. A two-phase tooth implant, which is free of gaps and capable of being steplessly positioned in its rotational orientation and which is stable towards rotational forces, comprising;

a first implant component with a top, and a bottom, an inner surface and an outer surface which is capable of being inserted into the jawbone, wherein the inner surface forms an tapered conical central seating opening at said top of said first implant component and wherein said inner surface forms a blind bore below said central seating opening wherein said blind bore has threads on the inner surface which are capable of accepting a screw, and a second implant component with a top portion and a bottom portion, an inner surface and an outer surface, the top portion further comprising a conical seating element for a dental prothesis with a central axis and the bottom portion further comprising a conical part having a central axis which interrelates with said central seating opening of said first implant component, said second implant component further forming a central bore passing coaxially through the bottom portion and through the top portion, and containing a tension screw with a top end, a bottom end, and a shaft, the top end having a broadened head and the bottom end having an outside fastening thread which fits into said threads on said inner surface of said blind bore of said first implant component to fasten said first implant component to said second implant component.

2. The tooth implant according to claim 1, wherein the axes of the conical seating element and the conical part of said second implant component are aligned with each other.

3. The tooth implant according to claim 1, wherein the axes of the conical seating element and the conical part of said second implant component are at an angle to each other.

4. The tooth implant according to claim 1, wherein said central bore is widened within the end directed towards the mouth cavity so that the head of said tension screw is seated within said central bore.

5. The tooth implant according to claim 1, wherein said first implant component has a cylindrical outer form with a spherically rounded end and a thread with a varying flank depth, the form of the thread flanks varying continuously upwards from the end embedded in the bone towards the seating opening.

6. The tooth implant according to claim 5, wherein said thread flank which points upwards towards the seating opening is formed as a plane surface and the thread flank which points downwards, varying in form, has a curved, concave shape.

7. The tooth implant according to claim 1, wherein the outer surface of said conical seating opening of said first implant component forms a first angle and the outer surface of said conical part of said second implant component forms a second angle whereby said first angle and said second angle are selected so as to produce a self-locking cone joint.

8. The tooth implant according to claim 7, wherein said angles are different.

9. The tooth implant according to claim 1, wherein said broadened head of said tension screw is irreversibly connected to the shaft.

10. A two-phase tooth implant kit, comprising;

a first implant component with a top, and a bottom, an inner surface and an outer surface which is capable of being inserted into the jawbone, wherein the inner surface forms an tapered conical central seating opening at said top of said first implant component and wherein said inner surface forms a blind bore below said central seating opening wherein said blind bore has threads on the inner surface which are capable of accepting a screw, and a second implant component with a top portion and a bottom portion, an inner surface and an outer surface, the top portion further comprising a conical seating element for a dental prothesis with a central axis and the bottom portion further comprising a conical part having a central axis which interrelates with said central seating opening of said first implant component, said second implant component further forming a central bore passing coaxially through the bottom portion and through the top portion, and a tension screw with a top end, a bottom end, and a shaft, the top end having a broadened head and the bottom end having an outside fastening thread which fits into said threads on said inner surface of said blind bore of said first implant component to fasten said first implant component to said second implant component.

11. A method for anchoring individual teeth or dental prosthesis, comprising;

inserting a two-phase dental implant into a jawbone, wherein in said two-phase dental implant comprises, a first implant component with a top, and a bottom, an inner surface and an outer surface which is capable of being inserted into the jawbone, wherein the inner surface forms an tapered conical central seating opening at said top of said first implant component and wherein said inner surface forms a blind bore below said central seating opening wherein said blind bore has threads on the inner surface which are capable of accepting a screw, and a second implant component with a top portion and a bottom portion, an inner surface and an outer surface, the top portion further comprising a conical seating element for a dental prothesis with a central axis and the bottom portion further comprising a conical part having a central axis which interrelates with said central seating opening of said first implant component, said second implant component further forming a central bore passing coaxially through the bottom portion and through the top portion, and containing a tension screw with a top end, a bottom end, and a shaft, the top end having a broadened head and the bottom end having an outside fastening thread which fits into said threads on said inner surface of said blind bore of said first implant component to fasten said first implant component to said second implant component, and seating said conical part of said second implant component in said central seating opening of said first implant element, adjusting the position of said second implant component relative to said first implant component.

* * * * *